US00PP20021P2

(12) United States Plant Patent
Wood

(10) Patent No.: US PP20,021 P2
(45) Date of Patent: May 26, 2009

(54) ***WEIGELA* PLANT NAMED 'BETH'**

(50) Latin Name: *Weigela florida*
Varietal Denomination: Beth

(75) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 12/075,451

(22) Filed: Mar. 11, 2008

(51) Int. Cl.
*A01H 5/00* (2006.01)

(52) U.S. Cl. ..... Plt./226
(58) Field of Classification Search ..... Plt./226
See application file for complete search history.

*Primary Examiner*—S. B McCormick Ewoldt
(74) *Attorney, Agent, or Firm*—C. A. Whealy

(57) ABSTRACT

A new and distinct cultivar of *Weigela* plant named 'Beth', characterized by its compact and uniform plant habit; freely branching habit; leaves with undulating margins; developing leaves with red-colored margins and fully expanded leaves that become brighter green in color with yellow green-colored venation during the late summer; red purple-colored flowers; and good garden performance.

2 Drawing Sheets

Figure 1:
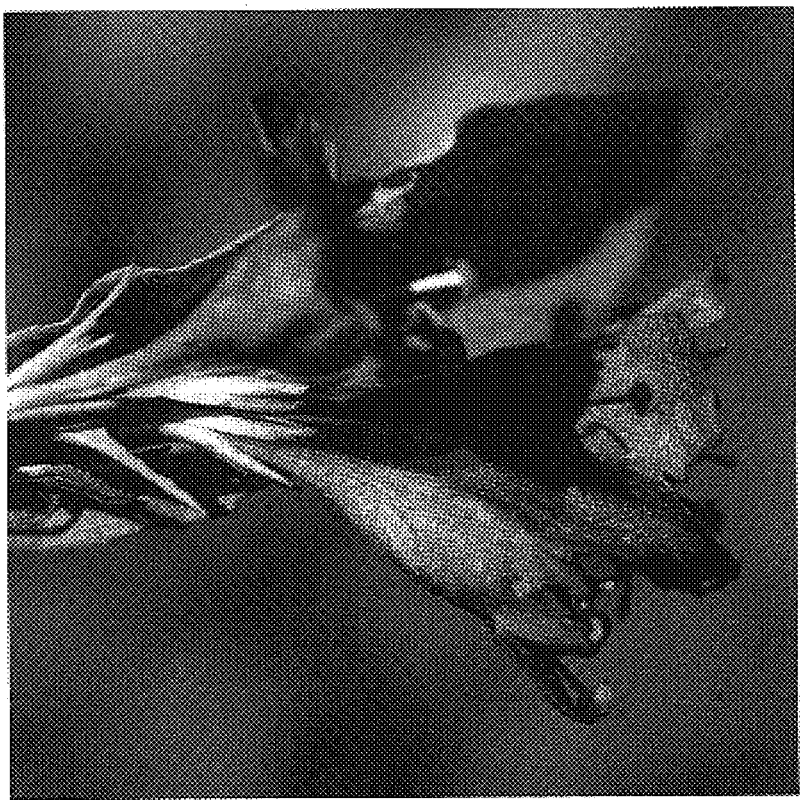
Figure 2:
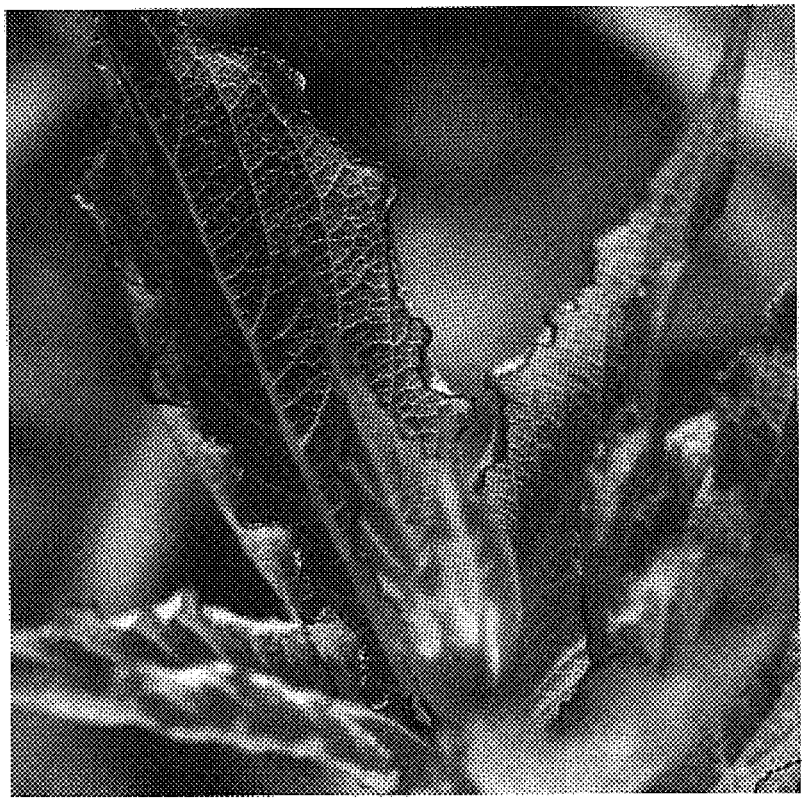

Botanical designation: *Weigela florida.*
Cultivar denomination: 'Beth'.

BACKGROUND OF THE INVENTION

The present invention relates to a new and distinct cultivar of *Weigela* plant, botanically known as *Weigela florida,* and hereinafter referred to by the name 'Beth'.

The new *Weigela* is a product of a planned breeding program conducted by the Inventor in Grand Haven, Mich. The objective of the breeding program was to develop new *Weigelas* with unique leaf shapes and coloration, uniform plant habit and hardiness.

The new *Weigela* originated from an open-pollination in 2004 of the *Weigela florida* cultivar Rubidor, not patented. The cultivar Beth was discovered and selected by the Inventor in 2005 as a flowering plant within the progeny of the stated open-pollination in a controlled environment in Grand Haven, Mich. Asexual reproduction of the new cultivar by cuttings in Grand Haven, Mich. since 2005 has shown that the unique features of this new *Weigela* plant are stable and reproduced true to type in successive generations of asexual reproduction.

SUMMARY OF THE INVENTION

The following traits have been repeatedly observed and are determined to be the unique characteristics of 'Beth'. These characteristics in combination distinguish 'Beth' as a new and distinct cultivar of *Weigela:*

1. Compact and uniform plant habit.
2. Freely branching habit.
3. Leaves with undulating margins.
4. Developing leaves with red-colored margins and fully expanded leaves that become brighter green in color with yellow green-colored venation during the late summer.
5. Red purple-colored flowers.
6. Good garden performance.

In side-by-side comparisons in Grand Haven, Mich. under commercial practice, plants of the new *Weigela* differ from plants of the female parent, the cultivar Rubidor, in the following characteristics:

1. Plants of the new *Weigela* have undulating leaf margins whereas plants of the cultivar Rubidor do not have undulating leaf margins.
2. Plants of the new *Weigela* and the cultivar Rubidor differ in leaf color as plants of the cultivar Rubidor have developing leaves that do not have red-colored margins and have fully expanded leaves that are yellow in color.
3. Under high light conditions, leaves of plants of the new *Weigela* do not burn whereas leaves of plants of the cultivar Rubidor burn.

Plants of the new *Weigela* can be compared to plants of the *Weigela florida* cultivar Variegata, not patented. In side-by-side comparisons in Grand Haven, Mich., plants of the new *Weigela* differ from plants of the cultivar Variegata in the following characteristics:

1. Plants of the new *Weigela* have undulating leaf margins whereas plants of the cultivar Variegata do not have undulating leaf margins.
2. Plants of the new *Weigela* and the cultivar Variegata differ in leaf coloration as plants of the cultivar Variegata have variegated leaves.
3. Plants of the new *Weigela* and the cultivar Variegata differ in flower color as plants of the cultivar Variegata have light pink and white-colored flowers.

BRIEF DESCRIPTION OF THE PHOTOGRAPHS

The accompanying colored photographs illustrate the overall appearance of the new *Weigela,* showing the colors as true as it is reasonably possible to obtain in colored reproductions of this type. Colors in the photographs may differ slightly from the color values cited in the detailed botanical description which accurately describe the colors of the new *Weigela.*

The photograph on the first sheet comprises a side perspective view of a typical plant of the cultivar Beth.

The photograph at the top of the second sheet is a close-up view of typical flowers of the cultivar Beth.

The photograph at the bottom of the second sheet is a close-up view of typical leaves of the cultivar Beth.

DETAILED BOTANICAL DESCRIPTION

The new *Weigela* has not been observed under all possible environmental conditions. The phenotype may vary somewhat with variations in environment such as temperature and light intensity, without, however, any variance in genotype. The aforementioned photographs, following observations and measurements describe plants grown during the spring and early summer in Grand Haven, Mich., in an outdoor nursery and under commercial production practices. Plants were about three years old when the photographs and description were taken. In the following description, color references are made to The Royal Horticultural Society Colour Chart, 1995 Edition, except where general terms of ordinary dictionary significance are used.

Botanical classification: *Weigela florida* cultivar Beth.

Parentage:

*Female or seed, parent.*—*Weigela florida* cultivar Rubidor, not patented.

*Male or pollen, parent.*—Unknown selection of *Weigela florida,* not patented.

Propagation:

*Type.*—By softwood cuttings.

*Time to initiate roots.*—About 15 days at temperatures of 22° C.

*Time to produce a rooted young plant.*—About two months at temperatures of 22° C.

*Root description.*—Fine, fibrous.

*Rooting habit.*—Freely branching; dense.

Plant description:

*Plant and growth habit.*—Perennial shrub. Compact and uniform plant habit; roughly spherical in shape. Vigorous growth habit. Freely branching habit with about 24 lateral branches developing per plant; pinching enhances lateral branch development.

*Plant height.*—About 57 cm.

*Plant diameter.*—About 60 cm.

Lateral branch description:

*Length.*—About 50 cm.

*Diameter.*—About 5 mm.

*Internode length.*—About 9 cm.

*Strength.*—Strong.

*Aspect.*—Erect to about 45° from vertical.

*Texture.*—Pubescent.

*Color, developing stems.*—145B.

*Color, mature stems.*—197B.

Foliage description:

*Arrangement.*—Opposite; simple.

*Length.*—About 13 cm.

*Width.*—About 5 cm.

*Shape.*—Elliptic to ovate/oblong.

*Apex.*—Acute to acuminate.

*Base.*—Cuneate.

*Margin.*—Serrulate; undulating.

*Texture, upper surface.*—Rugose, glabrous.

*Texture, lower surface.*—Rugose, pubescence at veins.

*Venation pattern.*—Pinnate.

*Color.*—Developing foliage, upper surface: 145A; at the margins, 181A. Developing foliage, lower surface: 145B; at the margins, 181A. Fully expanded foliage, upper surface: During the spring and early summer, 148B; late summer, color becoming closer to 146A; venation, 145B. Fully expanded foliage, lower surface: During the spring and early summer, 145B; late summer, color becoming closer to 146A; venation, 145B.

*Petiole.*—Length: About 9 mm. Diameter: About 4 mm. Texture, upper and lower surfaces: Smooth, glabrous. Color, upper and lower surfaces: 145B.

Flower description:

*Flower arrangement and habit.*—Funnelform flowers arranged in clusters of about seven flowers. Flowers not persistent. Flowers face upright, outwardly or are drooping.

*Fragrance.*—None detected.

*Natural flowering season.*—Plants of the new *Weigela* flower from May to June in Grand Haven, Mich.

*Flower longevity.*—Flowers last about six to eight weeks on the plant.

*Flower diameter.*—About 3 cm.

*Flower length* (*height*).—About 3.5 cm.

*Flower bud.*—Shape: Oblong. Length: About 1 cm. Diameter: About 4 mm. Color: 60A.

*Corolla.*—Arrangement: Funnelform, five petals fused into a long tube with separate petal lobes. Petal lobe length: About 1.6 cm. Petal lobe width: About 1.3 cm. Petal lobe shape: Roughly orbicular. Petal lobe apex: Acute. Petal lobe margin: Entire. Petal texture, upper and lower surfaces: Smooth, glabrous. Color: Petal, when opening, upper surface: 60A. Petal, when opening, lower surface: 60B. Petal, fully opened, upper surface: 60C; color becoming closer to 63B with development. Petal, fully opened, lower surface: 60B.

*Sepals.*—Quantity per flower: Five. Length: About 9 mm. Width: About 1 mm. Shape: Lanceolate. Apex: Acuminate. Margin: Entire. Sepal texture, upper and lower surfaces: Smooth; glabrous. Color, upper and lower surfaces: 155C.

*Peduncles.*—Length: About 8 cm. Diameter: About 1.7 mm. Angle: Erect to about 30° from stem axis. Strength: Moderately strong. Texture: Smooth, glabrous. Color: 145A.

*Pedicels.*—Length: About 1.6 cm. Diameter: About 2 mm. Angle: Erect to about 45° from stem axis. Strength: Moderately strong. Texture: Smooth, glabrous. Color: 145A.

*Reproductive organs.*—Stamens: Quantity/arrangement: Five per flower. Anther shape: Oblong. Anther length: About 5 mm. Anther color: 155A. Pollen amount: Moderate. Pollen color: 155A. Pistils: Quantity: One per flower. Pistil length: About 4 cm. Style length: About 3.8 cm. Style color: 158A. Stigma color: 158A. Seeds: Length: Less than 0.5 mm. Diarneter: Less than 0.5 mm. Color: Close to 200A.

Garden performance: Plants of the new *Weigela* have exhibited good tolerance to rain and wind and have been observed to tolerate temperatures from about −27° C. to about 37° C.

Pathogen/pest resistance: Plants of the new *Weigela* have not been observed to be resistant to pests and pathogens common to *Weigela.*

It is claimed:

1. A new and distinct *Weigela* plant named 'Beth' as illustrated and described.

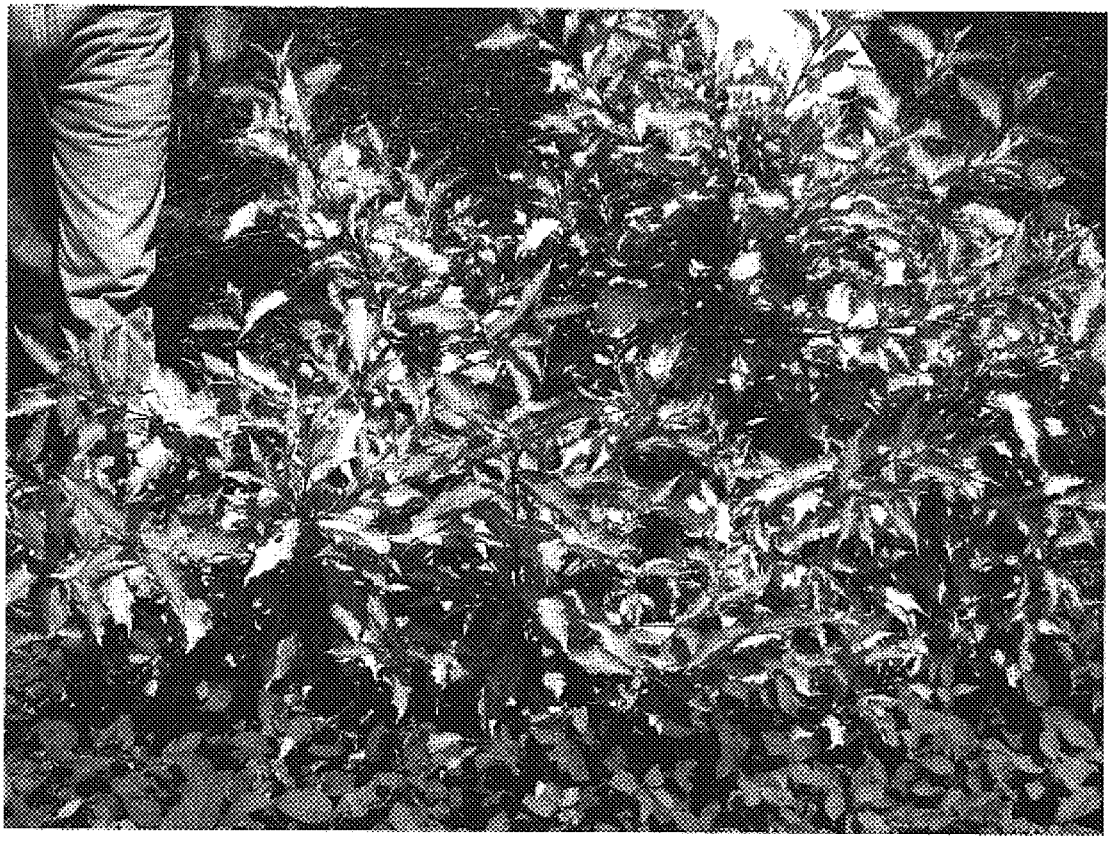

* * * * *